United States Patent [19]

Byun

[11] Patent Number: 5,243,968
[45] Date of Patent: Sep. 14, 1993

[54] PORTABLE VACUUM MASSAGE DEVICE

[76] Inventor: Kyoung S. Byun, Chukong Apt. 525-108, 27,, Chamsil-Dong Songpa-Ku, Seoul, Rep. of Korea

[21] Appl. No.: 890,653

[22] Filed: May 27, 1992

[51] Int. Cl.⁵ .......................... A61H 1/00; A61F 5/00
[52] U.S. Cl. ................................... 128/40; 128/24 R; 128/44; 600/38
[58] Field of Search ........................ 128/38–40, 128/64, 24.2, 44; 600/38–41; 137/844, 849; 417/437, 442, 118, 474; 119/14.02, 14.01, 14.22, 14.23

[56] References Cited

U.S. PATENT DOCUMENTS

| | | | |
|---|---|---|---|
| 1,059,070 | 4/1913 | Roberts | 417/442 X |
| 2,159,407 | 5/1939 | Seaman et al. | 137/849 X |
| 3,820,533 | 6/1974 | Jones | 600/38 |
| 4,111,192 | 9/1978 | Wu | 128/38 |
| 4,378,008 | 3/1983 | Osbon, Sr. | 600/38 |
| 4,856,498 | 8/1989 | Osbon | 600/38 |
| 5,083,556 | 1/1992 | Osbon et al. | 600/39 |

Primary Examiner—Robert A. Hafer
Assistant Examiner—Brian E. Hanlon
Attorney, Agent, or Firm—James D. Hall; Thomas J. Dodd

[57] ABSTRACT

A novel vacuum massage device adapted for speedily massaging the male genital organ. The vacuum massage device comprises an elongated cylindrical receptacle having first and second ends, a deformable cone-shaped member detachably coupled to the first end of the receptacle and having an opening provided at the central region thereof, and a pump mechanism coupled to the second end of the receptacle via a flexible hose for producing a vacuum within the receptacle. The receptacle includes a relief valve for controlling the vacuum produced therewithin.

3 Claims, 3 Drawing Sheets

PORTABLE VACUUM MASSAGE DEVICE

FIELD OF THE INVENTION

The present invention relates to a portable massage device; and, more particularly, to a high-speed vacuum massage device adapted for massaging a male genital organ by repetitively inflating and deflating same.

DESCRIPTION OF THE PRIOR ART

Diverse factors may be attributable to the malfunctioning of a male genital organ. Quite frequently, various physical or psychological disorders may produce a serious impairment to the virility of male sexuality. Accordingly, various exercise devices such as dildos and the like have been designed and used to aid sexual satisfaction or excitation during the sexual intercourse.

In addition, there have been proposed some massaging devices suitable for treating male impotence. For example, German Patent Nos. 825,137 and 835,637 disclose massaging apparatus for therapeutically treating the male genital by using a vacuum in an elastic cylindrical sleeve. However, such massaging apparatus have a disadvantage in that there is not provided means for controlling the vacuum in the sleeve. Therefore, an excessive or lesser vacuum may be generated in the sleeve, thereby diminishing substantially the effectiveness of the device.

In addition, German Laid-open Publication No. 25 28 093 offers another massaging apparatus including an elongated latex sleeve to be vibrated in the rotational and longitudinal directions by means of a vibrating device connected to one end thereof. In U.S. Pat. No. 4,580,553 issued to Laib, there is another massaging device for the therapeutic treatment of the male organ, which comprises a shape-retaining support tube and a soft-elastic molded body mounted in the support tube and driven in the longitudinal direction by a drive means. The manufacturing costs of such massaging apparatus are, however, relatively high as they are made not only in rather complicated structures but also of expensive parts including an electric motor and a driving device.

U.S. Pat. No. 4,748,973 discloses a pneumatic massage device for massaging a selected portion of the body, which comprises a suction cup member, a solenoid actuated vacuum pump for providing a vacuum within the cup member and a solenoid actuated needle valve for relieving the vacuum produced within the cup member. Such a pneumatic massage device may not be useful, however, for the purpose of massaging human genitals because of its structural characteristics. Also, an AC power source is required to operate the device, thereby inconveniencing the user for his need to gain access to a proper site.

SUMMARY OF THE INVENTION

Accordingly, it is an object of the present invention to provide a novel vacuum massage device which is portable, reliable, convenient, and enables a user to effectively and safely massage his genital organ in a minimal time.

It is another object of the present invention to provide a vacuum massage device for repetitively inflating and deflating the genital organ placed in an elongated cylindrical receptacle by a vacuum operation, thereby providing enhanced massaging effects.

It is a further object of the present invention to provide a vacuum massage device which comprises means for controlling a vacuum created within a receptacle during the massaging action.

The above and other objects of the present invention are accomplished by a vacuum massage device which comprises:

an elongated cylindrical receptacle having first and second ends, the first end having an open portion;

a deformable cone-shaped member detachably coupled to the first end of said cylindrical receptacle and having an opening provided at the central region thereof, wherein said cone-shaped member is adapted to be positioned in said cylindrical receptacle;

a flexible hose wherein one end thereof is detachably connected to the second end of said cylindrical receptacle;

pump means coupled to the other end of said flexible hose for producing a vacuum within said cylindrical receptacle, said pump means including a valve assembly adapted for streaming air in one way direction therethrough and a compressible elastic pocket coupled to the valve assembly, whereby the vacuum is produced within said cylindrical receptacle by repeated compressing and releasing operations of the pocket; and valve means provided at the second end of said cylindrical receptacle for controlling the vacuum produced within said cylindrical receptacle.

The valve assembly comprises a valve housing having a pair of spaced passageways formed therein, a first and a second check valves arranged in the respective passageways in a reverse relationship with each other and a valve cap rotatably coupled to an upper portion of the valve housing at a first and a second angular positions. The respective check valves are preferably made of elastic material, e.g., rubber. In addition, each of the check valves has a path formed therein and one or more slits traversing the path. Therefore, the slits of the check valves are easily expanded and closed in the compressing and the releasing operations of the elastic pocket, thereby enabling air to stream in one way direction via the paths because of the reverse alignment of the check valves.

The valve cap includes a projecting connector detachably coupled to the other end of the flexible hose and having an air passage provided therein which is adapted to alternatively communicate with one of the passageways of the valve housing by the rotation thereof. In addition, formed at the valve cap are a first and a second ports for providing selective communication with one of the first and the second passageways of the valve housing, respectively when the valve cap is rotated at the first and the second angular positions.

The valve means includes a valve casing provided at the second end of the cylindrical receptacle, a valve cover secured to the casing and having a hole in communication with atmospheric air and a relief valve disposed in the casing and biased by a spring for closing a valve port provided at the second end of the cylindrical receptacle. A rod from the relief valve extends through the hole of the valve cover and may be manually operated to overcome the spring force exerted on the valve, thereby enabling the valve to open the valve port. Therefore, a vacuum chamber of the receptacle can be in communication with atmospheric air via the valve port and the hole of the valve cover by pushing the valve rod in a lateral direction. In this case, air enters into the vacuum chamber, thereby lessening the vacuum produced within the receptacle.

BRIEF DESCRIPTION OF THE DRAWINGS

The above and other objects, advantages, and features of the invention will become apparent from the following description, taken in conjunction with the accompanying drawings.

DETAILED DESCRIPTION OF THE INVENTION

Figure 1:
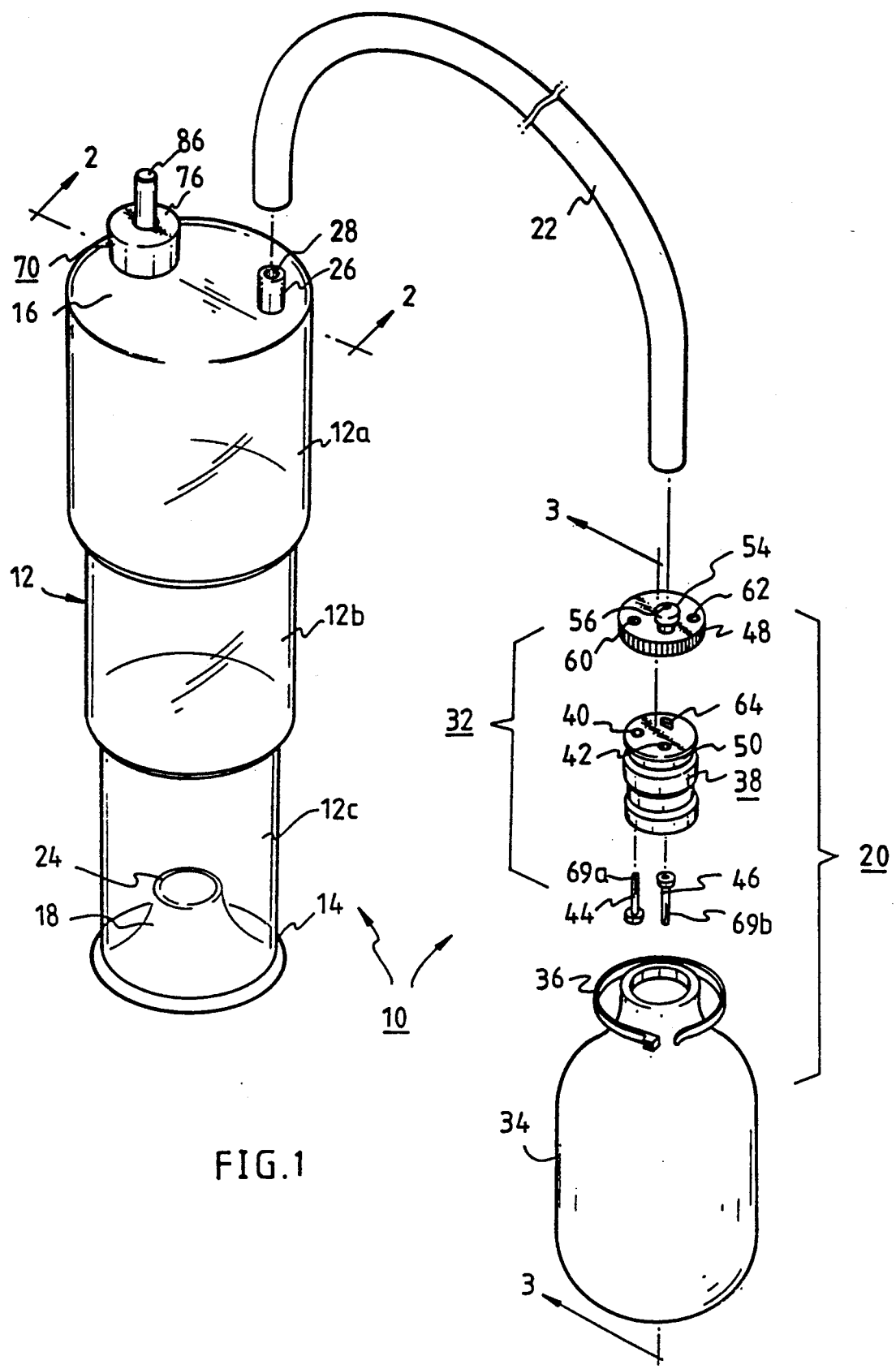
FIG. 1 is a partially exploded perspective view of a preferred vacuum massage device in accordance with the present invention.

Referring now to FIG. 1, there is shown a vacuum massage device 10 in accordance with a preferred embodiment of the present invention, which comprises an elongated cylindrical receptacle 12 having a first end 14 and a second end 16, the first end 14 having an open portion, a deformable cone-shaped member 18 detachably coupled to the first end 14 of the receptacle 12 and a manual vacuum pump 20 detachably coupled to the second end 16 of the receptacle 12 by a flexible hose 22. The cylindrical receptacle 12 is designed to receive various sizes of the human genital organs therein. The receptacle 12 may be assembled with three sections 12a, 12b, 12c as shown in FIG. 1. Preferably, the receptacle 12 is made of a transparent plastic material in order to enable the user to visually observe the massage action. The cone-shaped member 18 has an opening 24 provided at the central region thereof and adapted for passing the glans therethrough. The cone-shaped member 18 is preferably made of an elastic material such as silicone, rubber and the like. Therefore, the elastic deformation of the cone-shaped member 18 enables the member 18 to be easily placed in the cylindrical receptacle 12 in the massaging operation (see FIG. 1).

Figure 2:
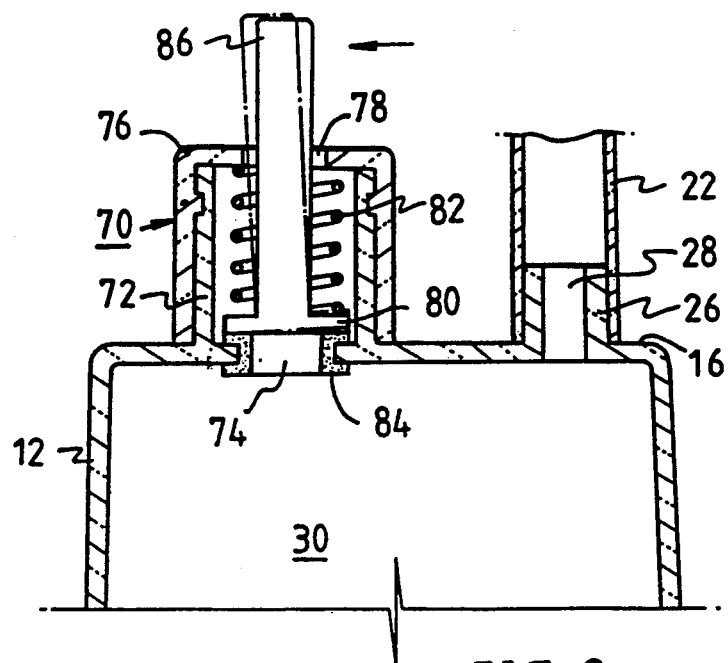
FIG. 2 is a partially sectional view taken along line 2—2 of FIG. 1 and shows valve means for controlling a vacuum produced within an elongated cylindrical receptacle of the massage device shown in FIG. 1, with certain parts broken away for clarity.

As shown in FIG. 2, provided at the second end 16 of the receptacle 12 is a ledge 26 coupled to one end of the flexible hose 22 and having an aperture 28 formed therein which provides air communication between the hose 22 and a vacuum chamber 30 of the receptacle 12.

Figure 3A:
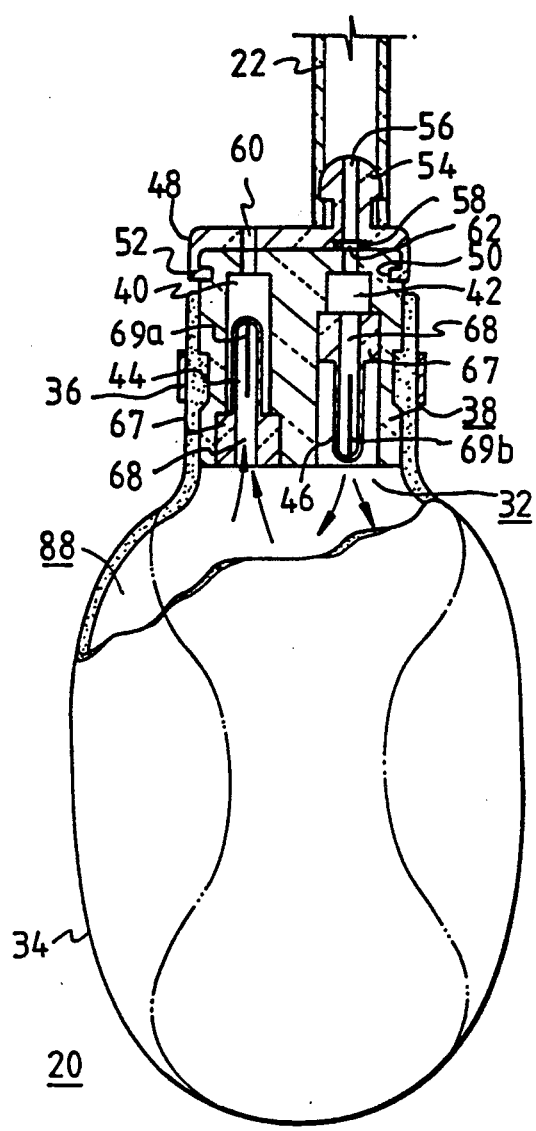
FIG. 3A is a sectional view taken along line 3—3 of the assembled massage device of FIG. 1 and shows pump means for producing a vacuum within the cylindrical receptacle shown in FIG. 1.
Figure 3B:
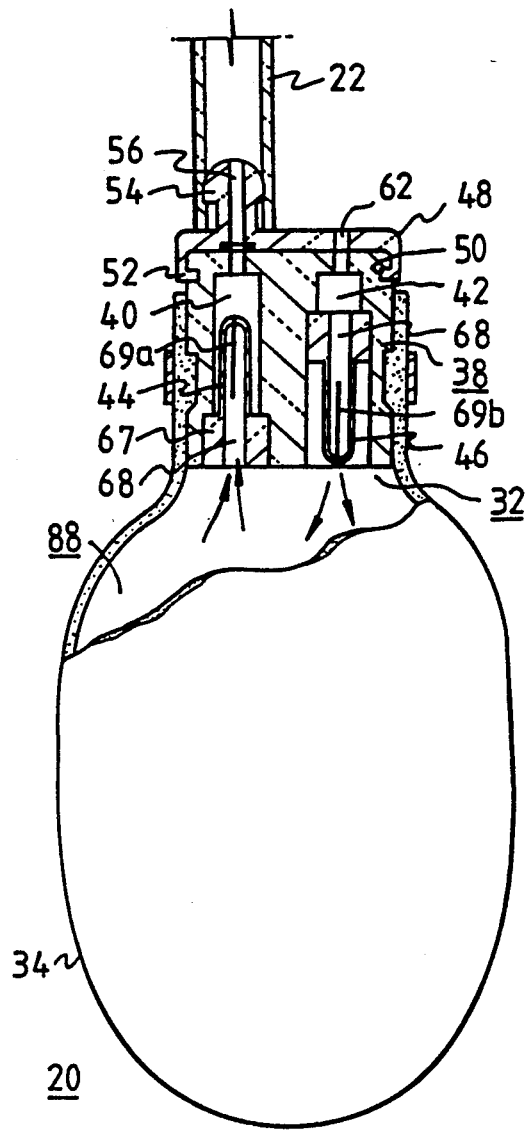
FIG. 3B is the same sectional view of the pump means as shown in FIG. 3A with a valve cap of the pump means rotated at a second angular position from its first position in FIG. 3A so as to remove the produced vacuum from the cylindrical receptacle of FIG. 1.

As shown in FIGS. 3A and 3B, the vacuum pump 20 includes a valve assembly 32 and a compressible pocket 34 coupled to the valve assembly 32 by a band 36. The pocket 34 is preferably made of an elastic material, e.g., rubber, silicone. Furthermore, in order to speedily produce a vacuum within the chamber 30 of the receptacle 12 by the repeated pumping operations of the pocket 34, preferably the compressed pocket 34 is momentarily recovered in its original shape upon releasing the pocket 34. The pocket 34 may be secured to the valve assembly 32 by using an adhesive.

The valve assembly 32 includes a valve housing 38 having a pair of spaced passageways 40, 42 provided therein, first and second check valves 44, 46 mounted in the respective passageways 40, 42 and arranged in a reverse relationship with each other and a valve cap 48 rotatably coupled to an upper portion of the valve housing 38. Provided at a circumferential surface of the valve housing 38 is an annular groove 50 complementary to a lug 52 formed at a lower portion of the valve cap 48. Therefore, the valve cap 48 is not easily separated from the valve housing 38 due to the coupling of the lug 52 to the groove 50. Integrally formed on the top surface of the valve cap 48 is a projecting connector 54 detachably coupled to the other end of the flexible hose 22. Also, provided in the projecting connector 54 is an air passage 56 which is in selective communication with one of the passageways 40, 42 by the rotation of the valve cap 48 as will be described hereinbelow. Preferably, seated in the bottom portion of the valve cap 48 near the air passage 56 is an O-ring 58 for providing the seal between the cap 48 and the valve housing 38.

In addition, as shown in FIGS. 1, 3A and 3B, the valve cap 48 has first and second ports 60, 62 which are in air communication with the first and the second passageways 40, 42 of the valve housing 38, respectively when it is rotated at a first and a second angular positions. Therefore, it is appreciated that the first and the second ports 60, 62 and the air passage 56 are arranged in a concentric relationship with each other with respect to the passageways 40, 42.

Figure 4:
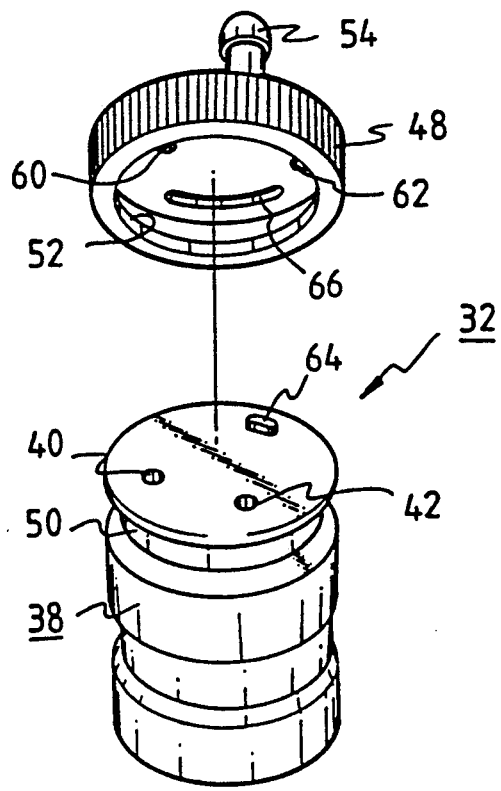
FIG. 4 is a perspective view of the inside of the valve cap shown in FIG. 1 and shows a curved slot of the valve cap slidably engaged with a pin provided at the top surface of a valve housing for stopping the rotation of the valve cap at the first and the second positions.

As best shown in FIG. 4, provided on the top surface of the valve housing 38 is a pin 64 which serves to stop the rotation of the valve cap 48 at the first and the second given angular positions. Formed at the inside of the valve cap 48 is a curved slot 66 within the range of a given rotational angle of the cap 48, which is slidably coupled to the pin 64. Therefore, the engagement of the slot 66 with the pin 64 enables the valve cap 48 to accurately stop at the first and the second angular positions, respectively when the valve cap 48 is rotated in the counterclockwise and the clockwise directions. As a result, the air passage 56 and the first port 60 can be connected to the second and the first passageways 42, 40 and the air passage 56 and the second port 62 to the first and the second passageways 40, 42, respectively when the valve cap 48 is moved in the first and the second angular positions as shown in FIGS. 3A and 3B.

The check valves 44, 46 are made of a flexible material, e.g., rubber as a cup shape. As shown in FIGS. 3A and 3B, the check valves 44, 46 include flanges 67 firmly held in the respective passageways 40, 42 and slits 69a, 69b traversing paths 68 thereof. The slits 69a, 69b are easily expanded and closed by the compressing and releasing operations of the pocket 34 because of the high flexibility of the check valves 44, 46, thereby providing the air flow or the air interruption between the passageways and the paths. As described above, since the check valves 44, 46 are disposed in the reverse relationship with each other, air stream can move, through the passageways 40, 42 of the valve housing 38 and the paths 68 of the check valves 44, 46, in one way direction as indicated in the arrows in FIGS. 3A and 3B when the vacuum pump 20 is operated.

As shown in FIGS. 1 and 2, provided at the second end 16 of the receptacle 12 is valve means 70 for manually controlling the vacuum produced within the chamber 30 of the receptacle 12 during the massaging operation. The valve means 70 includes a valve casing 72 having a valve port 74 provided at the second end 16 of the receptacle 12, a valve cover 76 secured to the casing 72 and having a hole 78 in communication with atmospheric air, and a relief valve 80 disposed in the casing 72 and adapted for closing the valve port 74. A spring 82 disposed in the casing 72 urges the valve 80 to close the valve port 74. Preferably provided at the valve port 74 is a valve seat 84 for enhancing the seal of the valve port 74. A valve rod 86 extends outward through the hole 78 of the valve cover 76 in order to facilitate the manual operation of the relief valve 80. It is preferable that a gap is provided in an appropriate distance between the hole 78 and the valve rod 86. As a result, the existence of the gap will cause atmospheric air to enter into the vacuum chamber 30 of the receptacle 12 via the valve port 74 when the valve 80 is opened by pushing the valve rod 86 in a lateral direction by hand as shown in phantom (see FIG. 2), thereby controlling the vacuum produced within the chamber 30.

In accordance with a preferred embodiment of the present invention, the action of massaging the object will be now described hereinbelow, with reference to the accompanying drawings.

Prior to the commencement of the massage action, as shown in FIG. 3A, the valve cap 48 is rotated at the first angular position, thereby allowing the air passage 56 and the first port 60 of the cap 48 to communicate with the second and the first passageways 42, 40, respectively. Therefore, the first port 60 is opened at the atmospheric pressure while the second port 62 is closed. Also, a massage cream is applied to the deformable cone-shaped member 18 and the object to be massaged in order to prevent the muscular and cellular tissue of the object from being injured during the massage action. Thereafter, the user operates the vacuum pump 20 by the manual manipulation, i.e., compresses and releases repeatedly the pocket 34 of the pump 20 after placing the glans into the opening 24 of the cone-shaped member 18. As consequently described, since the vacuum is produced within the chamber 30 of the receptacle 12 by the pumping operation of the pump 20, the object is sucked into the receptacle 12. In this connection, the slits 69a of the first check valve 44 are expanded while the slits 69b of the second check valve 46 are closed when the pocket 34 is compressed. Therefore, air is discharged from a chamber 88 of the pocket 34 to the atmosphere through the first check valve 44, the first passageway 40 of the valve housing 38 and the first port 60 of the cap 48.

In contrast, the slits 69a of the first check valve 44 are closed while the slits 69b of the second check valve 46 are expanded when the compressed pocket 34 is released. Therefore, air in the chamber 30 of the receptacle 12 is drawn into the pocket 34 through the flexible hose 22, the air passage 56 of the cap 48, the second passageway 42 of the valve housing 38 and the second check valve 46 in order. As a result, the repeated pumping operations of the pocket 34 produce speedily the vacuum within the chamber 30 of the receptacle 12, thereby inflating the object. At this time, it is necessary to periodically lessen the vacuum produced within the vacuum chamber 30 in order to prevent an excessive inflation of the object caused by an inordinate level of vacuum during the massage action. In this connection, pushing manually the valve rod 86 in the lateral direction will cause the valve 80 to open the valve port 74, atmospheric air being introduced into the vacuum chamber 30 via the hole 78 of the valve cover 76 to thereby relieve the vacuum. In addition, the relief valve 80 is instantly closed due to the spring force exerted thereon when the valve rod 86 is released. Therefore, such periodical manipulations of the pump 20 and the relief valve 80 will cause the object to be repeatedly inflated and deflated, thereby providing a massaging effect. The massage exercise may be preferably repeated 60–180 times, more preferably 80–120 times in about 3 minutes.

After the completion of massage, it is preferably to have the vacuum removed from the chamber 30 of the receptacle 12 so as to easily extract the receptacle from the massaged object. In this case, as shown in FIG. 3B, the valve cap 48 is placed at the second angular position by its clockwise rotation, thereby connecting the air passage 56 and the second port 62 of the cap 48 to the first and the second passageways 40, 42, respectively. Therefore, the first port 60 of the cap 48 is closed while the second port 62 is in communication with atmospheric air. As a result, atmospheric air is supplied into the chamber 30 of the receptacle 12 through the second and the first check valves 46, 44 and the hose 22 by the repeated pumping operations of the pump 20, thereby removing the vacuum produced within the chamber 30 of the receptacle 12. Furthermore, the continuous supply of air into the chamber 30 can facilitate the removal of the receptacle 12 from the massaged object. On the other hand, the vacuum may be removed from the chamber 30 by opening the relief valve 80.

While the present invention has been shown and described with reference to particular embodiments, it will be apparent to those skilled in the art that many changes and modifications may be made without departing from the spirit and scope of the invention as defined in the claims that follow.

What is claimed is:

1. A vacuum massage device adapted for massaging a male genital organ, which comprises:
   an elongated cylindrical receptacle having a first end and a second end, the first end having an open portion;
   a deformable cone-shaped member detachably coupled to the first end of said cylindrical receptacle and having an opening provided at a central region thereof, wherein said cone-shaped member is adapted to be positioned in said cylindrical receptacle;
   a flexible hose wherein one end thereof is detachably connected to the second end of said cylindrical receptacle;
   pump means coupled to the other end of said flexible hose for producing a vacuum within said cylindrical receptacle, said pump means including a valve assembly adapted for streaming air in a one way direction therethrough and a compressible elastic pocket coupled to the valve assembly, whereby the vacuum is produced within said cylindrical receptacle by repeated compressing and releasing operations of the pocket;
   said valve assembly including a valve housing having first and second passageways formed therein, first and second check valves mounted in the first and second passageways in a reverse relationship with each other for allowing air to flow in a one way direction through paths provided therein and having slits for providing an air communication between the passageways and the paths, a valve cap rotatably coupled to the valve housing and having an air passage and first and second ports provided therein wherein said valve cap is rotated at a first angular position at which the air passage and the first port thereof are in communication with the second and first passageways of the valve housing, respectively, and at a second angular position at which the air passage and the second port thereof are in communication with the first and second passageways, respectively, and means for stopping the rotation of said valve cap at the first and second positions; and valve means provided at the second end of said cylindrical receptacle for controlling the vacuum produced within said cylindrical receptacle.

2. The vacuum massage device of claim 1, wherein said stopping means includes a pin formed on the top surface of said valve housing, and a curved slot provided at the inside of said valve cap and slidably coupled to said pin of said valve housing.

3. The vacuum massage device of claim 2, wherein said valve means includes a valve casing provided at the second end of said receptacle and having a valve port in communication with a vacuum chamber of said receptacle, a relief valve disposed in said valve casing for opening and closing said valve port, a valve cover secured to said valve casing and having a hole adapted for freely passing a valve rod of said relief valve therethrough, and a spring disposed in said valve casing for urging said relief valve against said valve port.

* * * * *